US008571633B2

(12) United States Patent
Rosa

(10) Patent No.: US 8,571,633 B2
(45) Date of Patent: Oct. 29, 2013

(54) DIAGNOSTIC IMAGING METHOD

(76) Inventor: Scott Rosa, Rock Hill, NY (US)

( * ) Notice: Subject to any disclaimer, the term of this patent is extended or adjusted under 35 U.S.C. 154(b) by 877 days.

(21) Appl. No.: 12/409,355

(22) Filed: Mar. 23, 2009

(65) Prior Publication Data

US 2009/0240137 A1    Sep. 24, 2009

Related U.S. Application Data

(60) Provisional application No. 61/038,775, filed on Mar. 23, 2008.

(51) Int. Cl.
*A61B 5/05* (2006.01)
(52) U.S. Cl.
USPC ............ 600/411; 600/407; 600/410; 600/436
(58) Field of Classification Search
USPC ....................................................... 600/411
See application file for complete search history.

(56) References Cited

U.S. PATENT DOCUMENTS

| 5,099,859 | A | 3/1992 | Bell |
| 5,399,969 | A | 3/1995 | Bernstein |
| 5,762,608 | A | 6/1998 | Warne et al. |
| 5,807,255 | A | 9/1998 | Yokata et al. |
| 5,974,165 | A | 10/1999 | Giger et al. |
| 6,028,907 | A | 2/2000 | Adler et al. |
| 6,256,374 | B1 | 7/2001 | Tomasetti et al. |
| 6,490,475 | B1 | 12/2002 | Seeley et al. |
| 6,677,753 | B1 | 1/2004 | Danby et al. |
| 6,799,066 | B2 | 9/2004 | Steines et al. |
| 6,828,792 | B1 | 12/2004 | Danby et al. |
| 6,943,549 | B2 | 9/2005 | Matsup et al. |
| 7,196,519 | B2 * | 3/2007 | Damadian ................. 324/318 |
| 7,295,691 | B2 | 11/2007 | Uppaluri et al. |
| 2002/0198447 | A1 * | 12/2002 | Van Muiswinkel et al. .. 600/410 |
| 2003/0088174 | A1 | 5/2003 | Sussman et al. |
| 2003/0181808 | A1 * | 9/2003 | McKinnon ................. 600/411 |
| 2004/0044279 | A1 | 3/2004 | Lewin et al. |
| 2007/0100226 | A1 | 5/2007 | Yankelevitz et al. |
| 2008/0181470 | A1 * | 7/2008 | Camus et al. ............ 382/128 |

FOREIGN PATENT DOCUMENTS

JP    08191820 A2    7/1996

OTHER PUBLICATIONS

Eorthopod, A patient's guide to cervical whiplash, http://www.eorthopod.com/sites/default/files/Whiplash.pdf, 2003.*
Roberts et al, Vertebral Morphometry: Semiautomatic Determination of Detailed Shape From Dual-Energy X-ray Absorptiometry Images Using Active Appearance Models, Investigative Radiology, 41(12): 849-859, 2006.*
Krankenes et al, MRI of the tectorial and posterior atlanto-occipital membranes in the late stage of whiplash injury, Neuroradiology (2003) 45:585-591.

(Continued)

*Primary Examiner* — Unsu Jung
*Assistant Examiner* — Saurel J Selkin
(74) *Attorney, Agent, or Firm* — Edward S. Sherman

(57) ABSTRACT

A method of identifying injury to soft connective tissues in complicated body joints deploys use of motion x-ray images as the joint moves to identify suspected abnormal pathology followed by Dynamic Upright MRI images of the joint under conditions that express the abnormal pathology. The Dynamic Upright MRI parameters are based on the suspected pathology. The method is particularly useful in detecting disco/ligamentous and other injuries that often times will not be visualized on conventional recumbent MRI, or static x-rays.

21 Claims, 11 Drawing Sheets

(56) References Cited

OTHER PUBLICATIONS

Kaale, et al, Head Position and Impact Direction in Whiplash Injuries: Associations with MRI-Verified Lesions of Ligaments and Membranes in the Upper Cervical Spine, Journal of Neurotrauma, v22, No. 11, 2005, pp. 1294-1302.

Krankenes et al, MRI assessment of the alar ligaments in the late stage of whiplash injury—a study of structural abnormalities and observer agreement, Neuroradiology (2002) 44:617-624.

Bergholm et al, New Diagnostic Tools Can Contribute to Better Treatment of Patients with Chronic Whiplash Disorders, Journal of Whiplash & Related Disorders, vol. 3(2) 2004, pp. 5-19.

De Boer, R., MRI stands out among soft tissue imaging innovations, IHE,—Issue N°7—Nov. 2006, pp. 42-43.

Bitterling H, et al., "Mystery of alar ligament rupture: value of MRI in whiplash injuries—biomechanical, anatomical and clinical studies", Rofo. Nov. 2007;179(11):1127-36. (which is not admitted as prior art by the applicant).

Vetti, N. et al., "MRI of the alar and transverse ligaments in whiplash-associated disorders (WAD) grades 1-2: high-signal changes by age, gender, event and time since trauma", Neuroradiology. Apr. 2009;51(4):227-35. Epub Dec. 16, 2008.

* cited by examiner

FIG. 4A is the Neutral posture sagital Motion X-ray frame, FIG. 4B is a photograph of the patients posture at the time FIG. 4A was acquired while FIG. 4C is the corresponding Sagital Upright MRI at the same posture as FIG. 4A and 4B.

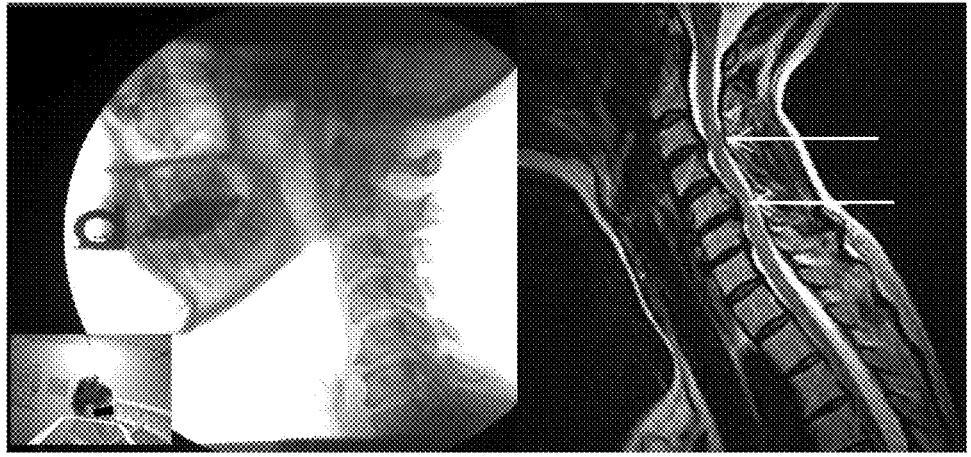
FIG. 5B   FIG. 5A Neutral Motion X-ray   FIG. 5C
Neutral Upright MRI
Disc herniation with spinal cord compression
T2 FSE spin sequence
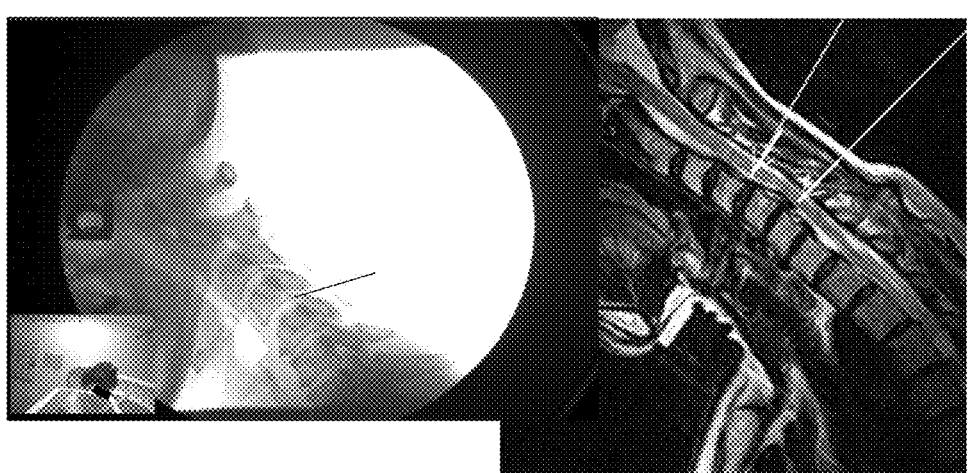
FIG. 6B
FIG. 6C:
Corresponding Flexion MRI
T2 FSE spin sequence
Fig 6A
Flexion Motion X-ray showing Anteriolisthesis (forward slipping) of C4-5
Line 601: Anteriolisthesis (forward slipping) of C4-5
Line 602 Torn Posterior Longitude Ligament

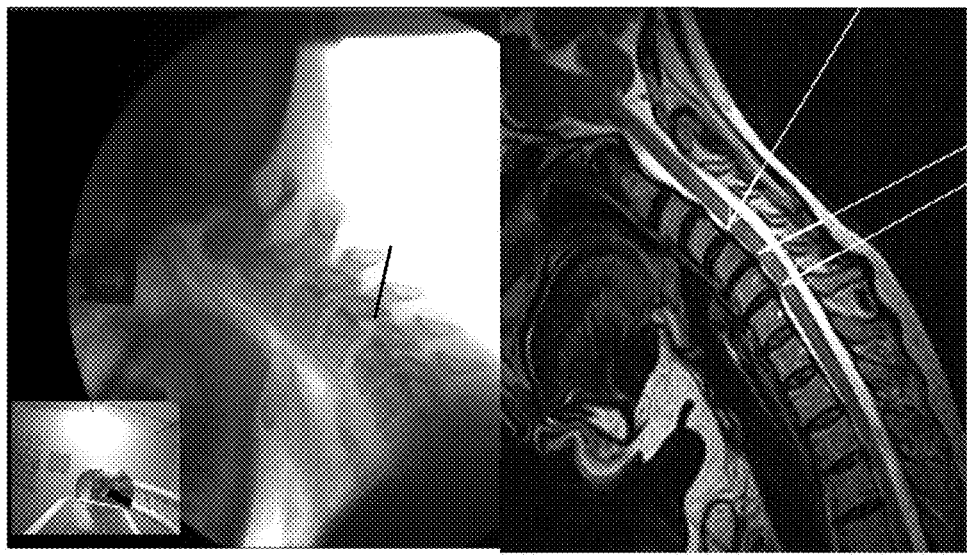

FIG. 7B positioning for Dynamic Upright MRI

FIG. 7A

Flexion position with Anteriolisthesis of C4-5

FIG. 7C Flexion MRI positionPatient
Line 701:Anteriolisthesis of C4-5

Lines 702 and 703: disc/spinal cord compression
T2 FSE spin sequence

T2 FSE spin sequence

FIG. 8B
Patient positioning for Dynamic Upright MRI

FIG. 8A Extension position

Retrolisthesis of C3-4 (backward slipping)

FIG. 8C
Extension position MRI

Line 801:Retrolisthesis of C3-4 (backward slipping)
Lines 802 and 803: disc/spinal cord compression

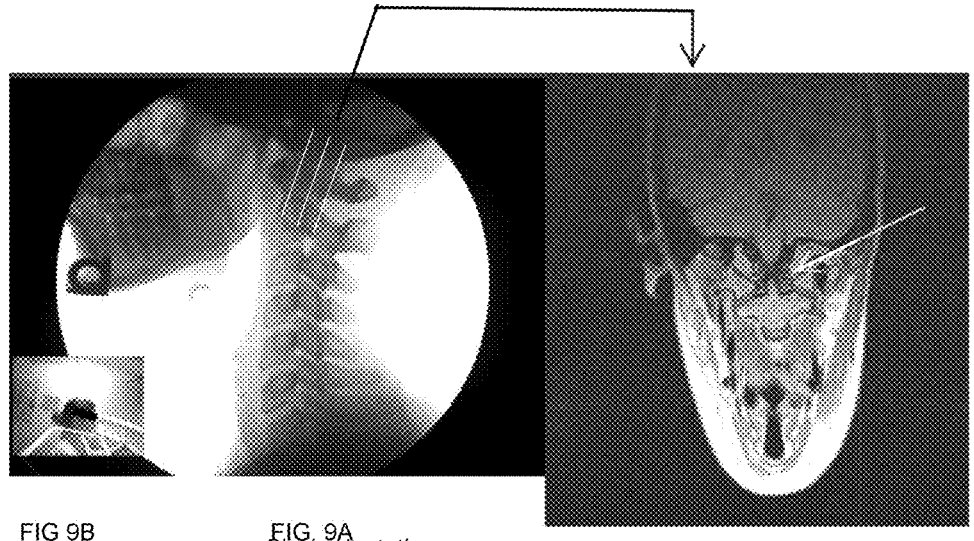

FIG 9B

Patient positioning for Dynamic Upright MRI

FIG. 9A
Slice orientation for Coronal images of alar and transverse ligaments
Neutral posture FIG. 9C Torn alar ligament PD weighted image

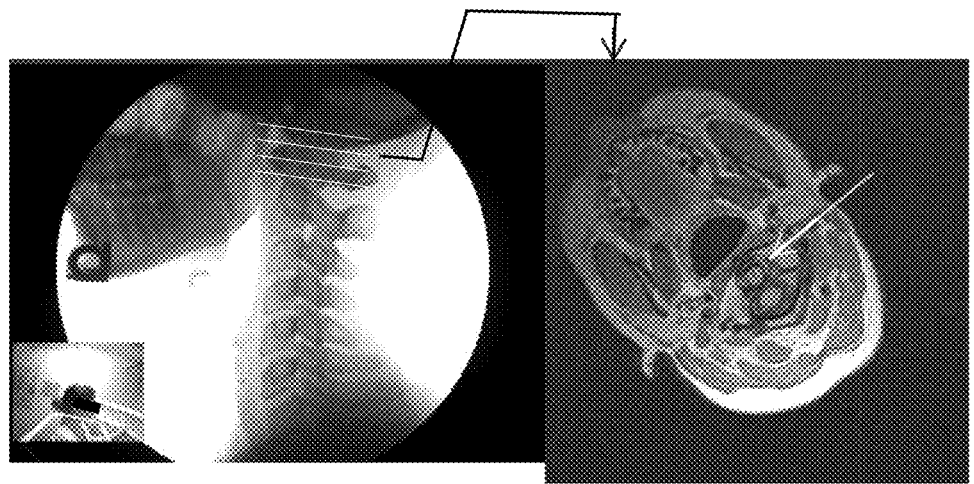

FIG. 10B

Patient positioning for Dynamic Upright MRI

FIG. 10A
Slice orientation for axial spot of the craniocervical junction for transverse and alar ligaments
Neutral posture

FIG. 10C

Torn transverse ligament
Head rotated, neutral posture, PD weighted image sequence

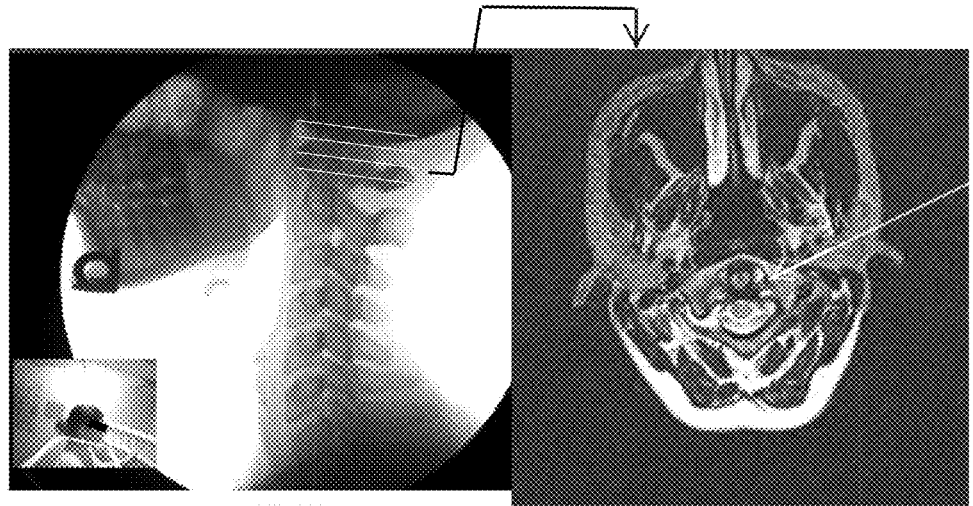

FIG.11A

Patient positioning for Dynamic Upright MRI

FIG.11B
Slice orientation for axial spot of the craniocervical junction for transverse and alar ligaments
Neutral position FIG. 11C
Torn transverse ligament Axial spot, neutral posture, T2 FSE sequence

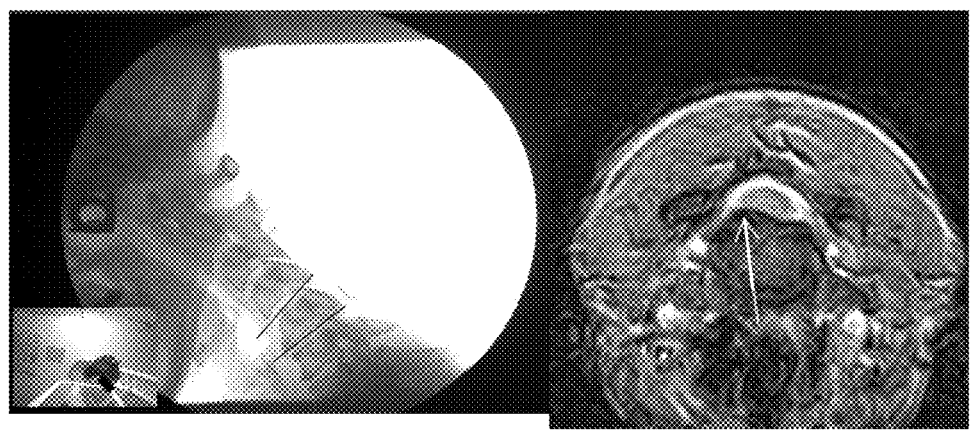

FIG. 12A

Patient positioning for Dynamic Upright MRI

FIG. 12B

Slice orientation for Axial spot of intervertebral disc in Flexion

FIG. 12C

Severe disc herniation with spinal cord and nerve root compression in flexion position Axial spot in flexion, GRE spin sequence Patient positioning for Dynamic Upright MRI Slice orientation for Axial spot of intervertebral disc in Extension Severe disc herniation with spinal cord and nerve root compression Axial spot in extension, GRE spin sequence

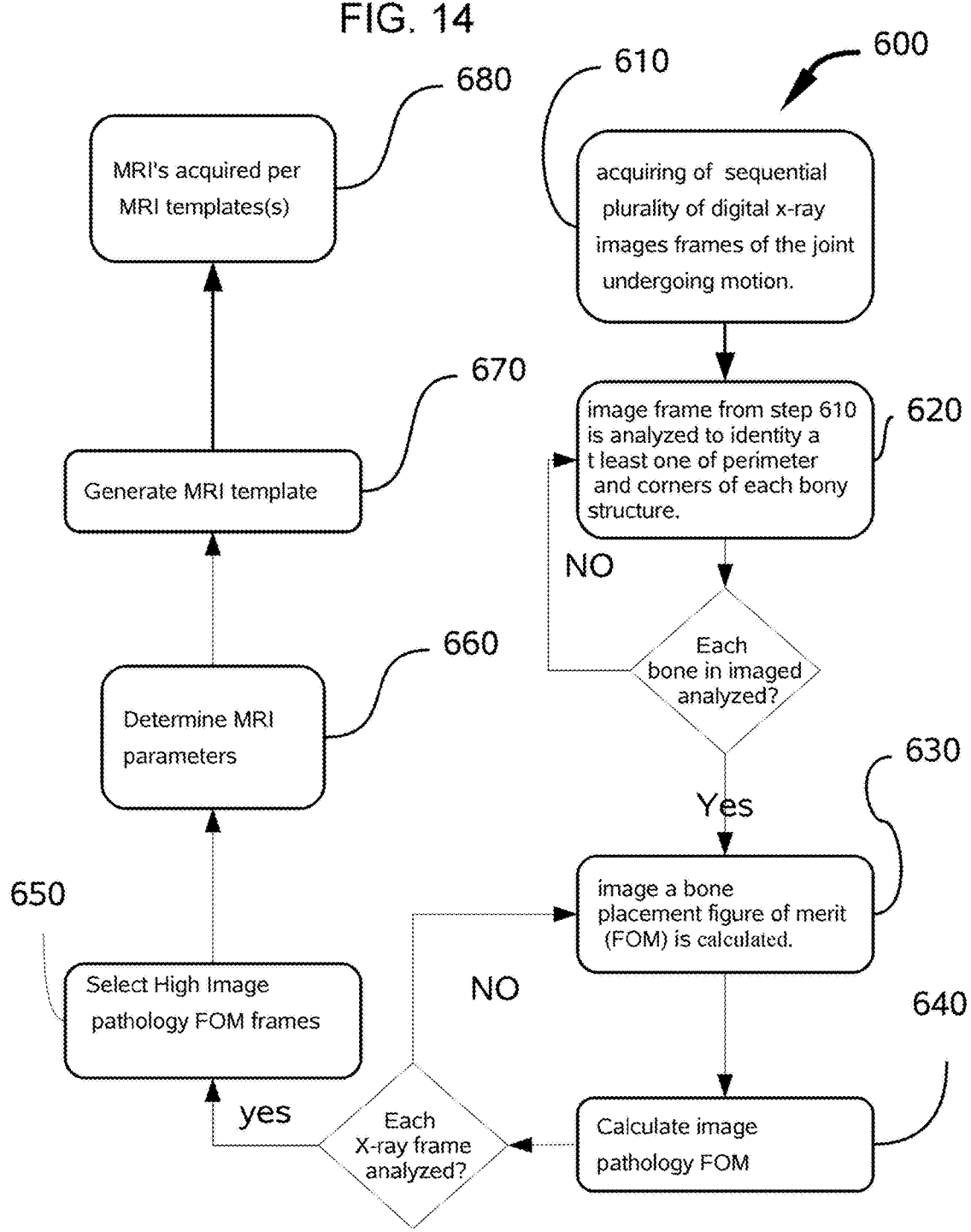

DIAGNOSTIC IMAGING METHOD

CROSS REFERENCE TO RELATED APPLICATIONS

The present application claims priority to the U.S. Provisional Patent Application of the same title having application Ser. No. 61/038,775 which was filed on Mar. 23, 2008 and is incorporated herein by reference.

BACKGROUND OF THE INVENTION

The present invention relates to radiological imaging, and in particular to methods of MRI imaging of soft tissue.

The limitations of conventional X-ray imaging in detecting and diagnosing soft tissue injuries, that is structures other than calcified bone, is well known. Soft tissue, being much less dense than bone, has either too low a contrast to be observed, or is obscured by the bone structures, as the x-ray itself is a projected image in which x-rays are attenuated as they pass through the patient.

Magnetic resonance imaging (MRI) provides images of tissues not generally visible in x-rays, as well as bone. Rather than the images being a projection through the tissue and organ from the front to the back of the image plane, as in conventional x-rays images, like Computed tomography (CT), MRI can be obtained of thin slices at different positions and orientations in any plane. Further, MR has much greater soft tissue contrast than CT making it especially useful in neurological, musculoskeletal, cardiovascular and oncological diseases. Unlike CT it uses no ionizing radiation. The scanner creates a powerful magnetic field which aligns the magnetization of hydrogen atoms in the body. Radio waves are used to alter the alignment of this magnetization. This causes the hydrogen atoms to emit a weak radio signal which is amplified by the scanner. This signal can be manipulated by additional magnetic fields to build up enough information to reconstruct an image of the body.

Magnetic Resonance Imaging while capable of imaging soft tissue, as currently practiced has numerous limitations in identifying soft tissue injuries. While improvements in MRI scanning techniques have reduced the acquisition time, imaging is still a serial technique where a slice of the patient is imaged by precise positioning of a magnetic field and the imposition of gradients onto the slice. Thus, MRI has the advantage over X-ray in that surrounding structure is eliminated, while X-ray are a projection, with denser tissue obscuring features in finer tissue. However, as one attempts to acquire a sequence of MRI images dynamically, with limited motion between them, the resolution is inherently reduced as the speed of acquisition is increased to acquire additional frames.

Unfortunately, a failure to find soft tissue injuries by MRI frequently leads to incorrect diagnosis, or the assumption that the patient is exaggerating about the symptoms of pain and discomfort, or are of a psychological rather than physical origin.

It is now appreciated, in light of the present invention, that because MRI is so specific and sensitive soft tissue injuries are more frequently missed than identified. The ability to know early on in a patient's injury on what exactly has been traumatized is likely to result in better clinical outcomes for patients, and less risk of further degeneration, progressive deterioration of a patient's condition from neglect or inappropriate treatments.

It is therefore a first object of the present invention to provide for the identification of soft tissue injuries that have been elusive to static conventional diagnostic imaging protocols.

It is a further object of the invention to avoid the waste of time and expense on unreasonable treatments and diagnostic studies that are made when soft tissue injury is overlooked or not fully understood.

It is a further object of the invention to provide for the assessment and evaluation of the soft tissue injuries in moving joints, and in particular injuries to the cervical spine. The proper assessment and evaluation directs the treating Physician into the best treatment/care plan necessary to help the injured patient, to minimize future pain and prevent treatments that can increase pain or cause further injury.

SUMMARY OF INVENTION

In the present invention, the first object is achieved by providing a medical imaging method for joints in living creatures, the method comprising the steps of: acquiring a dynamic sequence of x-ray images of at least one joint of a living creature over a range of motion, analyzing the dynamic x-ray image frames to identify positions and locations with possible abnormal pathology, determining MRI parameters for imaging the possible abnormal pathology in greater detail than the x-ray images, acquiring MRI images at positions and locations with abnormal pathology with said parameters.

The above and other objects, effects, features, and advantages of the present invention will become more apparent from the following description of the embodiments thereof taken in conjunction with the accompanying drawings.

BRIEF DESCRIPTION OF THE DRAWINGS

FIG. 4A is an x-ray of the cervical spine of the upright patient in a neutral posture frame while FIG. 4B is a photograph of the patient at the time the frame in FIG. 4A was acquired and FIG. 4C is the sagital MRI corresponding to the posture in FIG. 4A.

FIG. 5A is an x-ray frame of the cervical spine of the upright patient in a neutral posture frame while FIG. 5B is a photograph of the patient at the time the frame in FIG. 5A was acquired. FIG. 5C is the sagital MRI corresponding to the posture in FIG. 5A FIG. 6A is a frame of a dynamic x-ray sequence capturing the cervical spine of the upright patient in a flexion posture while FIG. 6B is a photograph of the patient at the time the frame in FIG. 6A was acquired and FIG. 6C is the sagital MRI corresponding to the posture in FIG. 6A FIG. 7A is a frame of a dynamic x-ray sequence capturing the cervical spine of the upright patient in a flexion posture while FIG. 7B is a photograph of the patient at the time the frame in FIG. 7A was acquired. FIG. 7C is the sagital MRI corresponding to the posture in FIG. 7A FIG. 8A is a frame of a dynamic x-ray sequence capturing the cervical spine of the upright patient in a extension posture while FIG. 8B is a photograph of the patient at the time the frame in FIG. 8A was acquired and FIG. 8C is the sagital MRI corresponding to the posture in FIG. 8A FIG. 9A is an x-ray frame of the cervical spine of the upright patient in a neutral posture frame while FIG. 9B is a photograph of the patient at the time the frame in FIG. 9A was acquired. FIG. 9C is an axial MRI image on the slice indicated on FIG. 6A

FIG. 10A is a frame of a dynamic x-ray sequence of the cervical spine of patient is in an upright posture capturing the right rotation of the head, FIG. 10B is a photograph of the patient at the time the frame in FIG. 10A was acquired. FIG. 10C is an axial MRI image on the slice indicated on FIG. 10A

FIG. 11A is an x-ray frame of the cervical spine of the upright patient in a neutral posture frame while FIG. 11B is a photograph of the patient at the time the frame in FIG. 11A was acquired. FIG. 11C is an axial MRI image on the slice indicated on FIG. 11A

FIG. 12A is a frame of a dynamic x-ray sequence capturing the cervical spine of the upright patient in a flexion posture while FIG. 12B is a photograph of the patient at the time the frame in FIG. 12A was acquired. FIG. 12C is an axial MRI image on the slice indicated on FIG. 12A

FIG. 13A is a frame of a dynamic x-ray sequence capturing the cervical spine of the upright patient in an extension posture while FIG. 13B is a photograph of the patient at the time the frame in FIG. 13A was acquired. FIG. 13C is an axial MRI image on the slice indicated on FIG. 13A

FIG. 14 is a flow chart for a computer aided application of the process.

DETAILED DESCRIPTION

Figure 1:
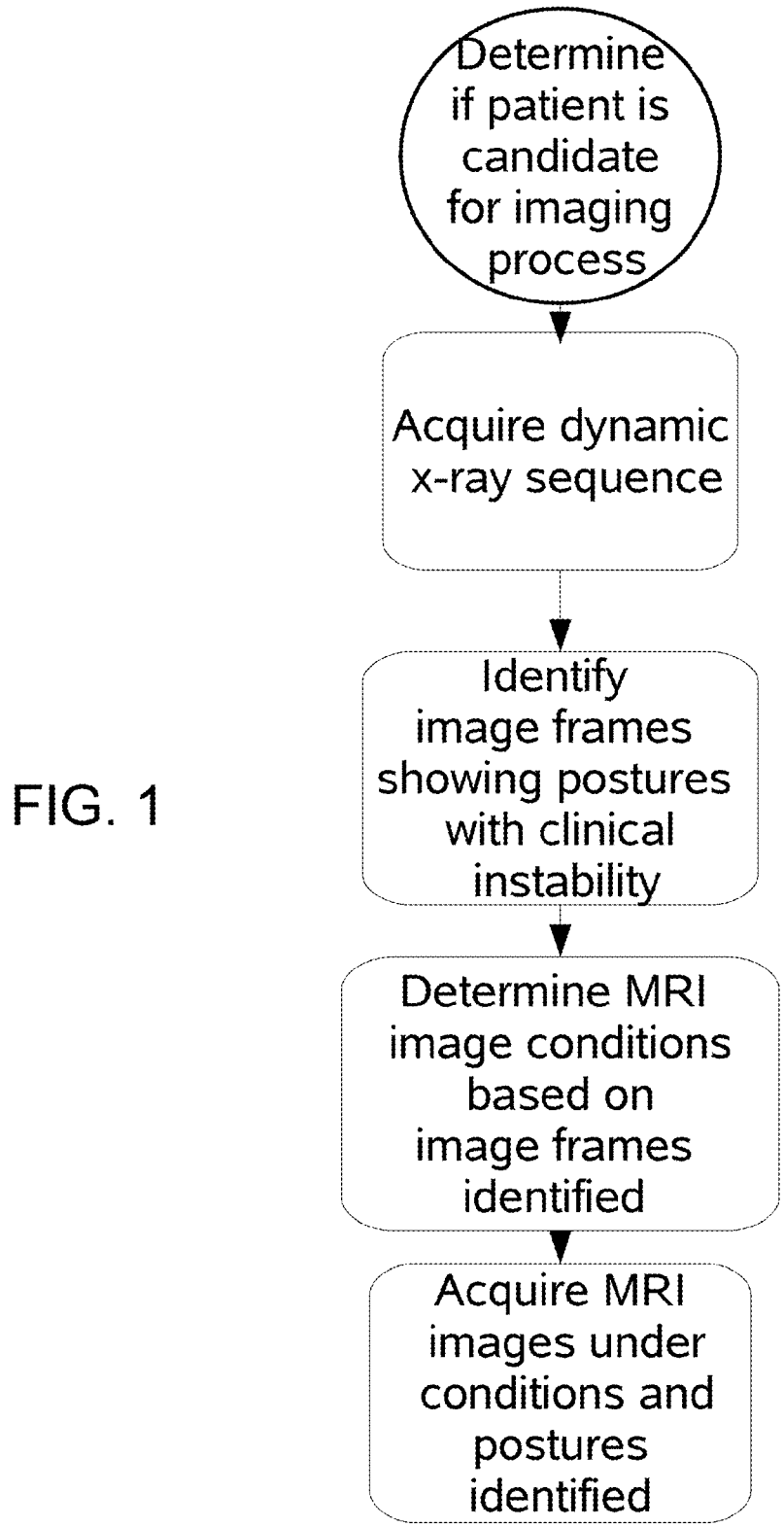
FIG. 1 is a flow chart of a first embodiment of the method

Referring to FIGS. 1 through 14, wherein like reference numerals refer to like components in the various views, there is illustrated therein a new and improved Diagnostic Imaging Method, generally denominated 100 herein.

In accordance with the present invention, the inventive process 100 as shown in FIG. 1 comprises a first step 110 of acquiring dynamic x-ray sequence of at least one joint of a living creature over a range of motion. In the first step, 110 x-ray images are continuously acquired in different views of the joint under investigation as the patient moves the joint in the different direction of normal motion. It is generally preferable the joint's are load bearing during all of the dynamic X-ray (step 110) and MRI imaging steps 140, however in some instances it may prove useful to obtain non-load bearing images by either static or dynamic x-ray or MRI.

The next step 120 in process 100 is analyzing the dynamic x-ray frames to identify positions and locations with abnormal pathoanatomy. The subsequent step 130 in process 100 is Determining of MRI parameters i.e. (which may include one or more of slice orientation, slice thickness, spin sequence and patient positioning, as further described below. The next step 140 is acquiring MRI images under these parameters at positions and locations with abnormal pathoanatomy with said parameters.

Various embodiments and results of the invention will now be illustrated with respect to the diagnosis of patients that have suffered a painful or other injury to the cervical spine, such as from a motor vehicle accident (MVA). In step 110, one or more series of x-rays images are acquired while the patient stands upright and move their head in the directions indicated by the technician, which generally include in addition to neutral sagital images, a sequence of images in front to back flexion, extension and side to side movement. Axial views are recorded during the front to back extension and flexion as well as anterior-posterior view is recorded during side to side motion. The x-rays are acquired very rapidly so that the patient can move the neck at normal speed but each x-ray image frame will show a relative small amount of motion with respect to the adjacent frames. As the patient is upright, the mass of the head places a load on the cervical spine.

Recent improvements in the digital acquisition of x-rays have enabled dynamic x-ray imaging where the clinician is able to see the bone structure in a joint as the patient moves, as well as capture a sequence of digital images of the joint under study in real time. Presently dynamic x-ray equipment is available from DMX Works, Inc., 4159-B Corporate Court Palm Harbor, Fla. 34683. Other means of digital x-ray image acquisition are described in the following U.S. Pat. Nos. 6,256,374 and 6,490,475, which are incorporated herein by reference.

In step 120, the full sequence of x-ray image frames acquired in step 110 is then reviewed by a physician to identify which postures indicate the most aberrant pathoantomy for positive findings of intersegmental joint dysfunction/instability. By aberrant pathoanotomy we mean postures that show an abnormal absolute and relative position of the cervical vertebrae with respect to each other, causing dysfunction or instability of intersegmental joints.

Although these selected X-ray images do not reveal the soft tissue damage itself they serve as a guide for subsequent MRI imaging, which if carried out according to the most preferred embodiment of the invention, will reproducibly reveal the actual soft tissue damage.

The next step 130 of determining the MRI conditions is based on the patient specific biomechanic assessment of vertebra posture and anatomy of the surrounding soft tissue.

Soft tissue damage when detected by MRI is generally apparent either because the soft tissue is torn, thinned, scarred or misplaced/disconnected. However, it has been discovered that these changes will generally not be apparent unless the MRI is acquired under the conditions that indicated abnormal pathology in the motion x-ray image series of step 110.

Hence, it is important in step 140 that the patient be positioned with nearly the identical posture during the MRI that indicated abnormal pathology in the motion x-ray frame selected in step 120 as showing the aberrant pathology.

Recent improvement in MRI technology, as disclosed in the following U.S. Pat. Nos. 7,196,519; 6,677,753; and 6,828, 792; which are incorporated herein by reference, have enabled commercial equipment for the acquisition of MRI in other than prone position, such as weight bearing position or any positions of a joint over a range of motion. Such equipment is currently available from Fonar Corporation 110 Marcus Drive, Melville, N.Y. 11747

Further, the proper areas of the tissue must be imaged. Because MRI is so precise in its ability to image sections of tissue, care must be taken to select the appropriate series of sections as well as acquire the images under conditions in which the suspected damaged tissue will stand out from adjacent tissue so that the diagnosis can be obtained. That is the radiologist analyzing the MRI images must be able to look at the right location to see the thinning, tears, scar or other damage to the precise soft tissue to diagnose the injury and source of pain. This particularly problematic because such damage may be present in any of the three dimensions the damaged tissues occupies and at any orientation, thus it will be difficult to capture in a 2-dimensional image acquired by MRI. Hence, prior MRI studies of a patient that did not show soft tissue damage can cause false negative results.

Thus, in order to overcome this difficulty it has been discovered that specific imaging conditions will accurately and reproducibly indicate the aforementioned tissue damage. However, these imaging conditions are specific to the pathology identified in the motion x-ray analysis of steps 110 and 120.

Table 1 discloses preferred combinations of MRI imaging modes and conditions in series of columns for the various cervical spine injuries common in MVA, as listed in the sequence rows.

The important imaging conditions listed in the first row of Table 1 is the patient's position or posture, the MRI slice orientation and the spin sequence and analysis method used by the MRI machine to create the contrast in the image. Generally, in all cases it is desirable to acquire MRI images under the conditions in the second row when the patient is upright, rather than prone or recumbent with the neck in a neutral posture (not bent in any direction) other neck positions are flexing forward or extending backward or titled to the side or with the mouth open. After these neutral posture images are obtained additional images are acquired according to the pathology identified in step 110, where the patient is placed in the same posture that resulted in the finding of abnormal pathology in step 120.

MRI imaging parameters are MRI slice orientation (stack positioning), slice thickness (for optimal ligamentous, joint dysfunction assessment), spin sequence (to view soft tissue with sequences best used to reveal soft tissue pathology) and where to specifically look for the lesion which had been found on the initial Motion X-Ray study of step 110.

The MRI slice orientation and position is either axial (looking down the spine) or sagittal (looking at the spine in profile) as well as centered on a particular bone or junction. Anterior to posterior view (AP) means facing the patient from the front so that the right and left sides are visible.

The images must be acquired in specific planes or slices where the abnormal pathology is likely to be visible based on the initial x-ray study. Generally, it is preferred that multiple slices are obtained; hence there is a need to determine the slice spacing and the number of slices.

It is also generally preferred in the inventive method that an x-ray image that shows the proper posture for the MRI images also be marked with one or more lines that indicate the desired MRI section locations. Such images that contain these marking will be referred to as templates. It is further preferred that the template also include a visual photograph of the patent that is recorded at the same instant the X-ray image was recorded. It is preferred that these images are provided as small inset images of reduced magnification at the corner of template where it will not obscure important anatomical features.

Figure 2:
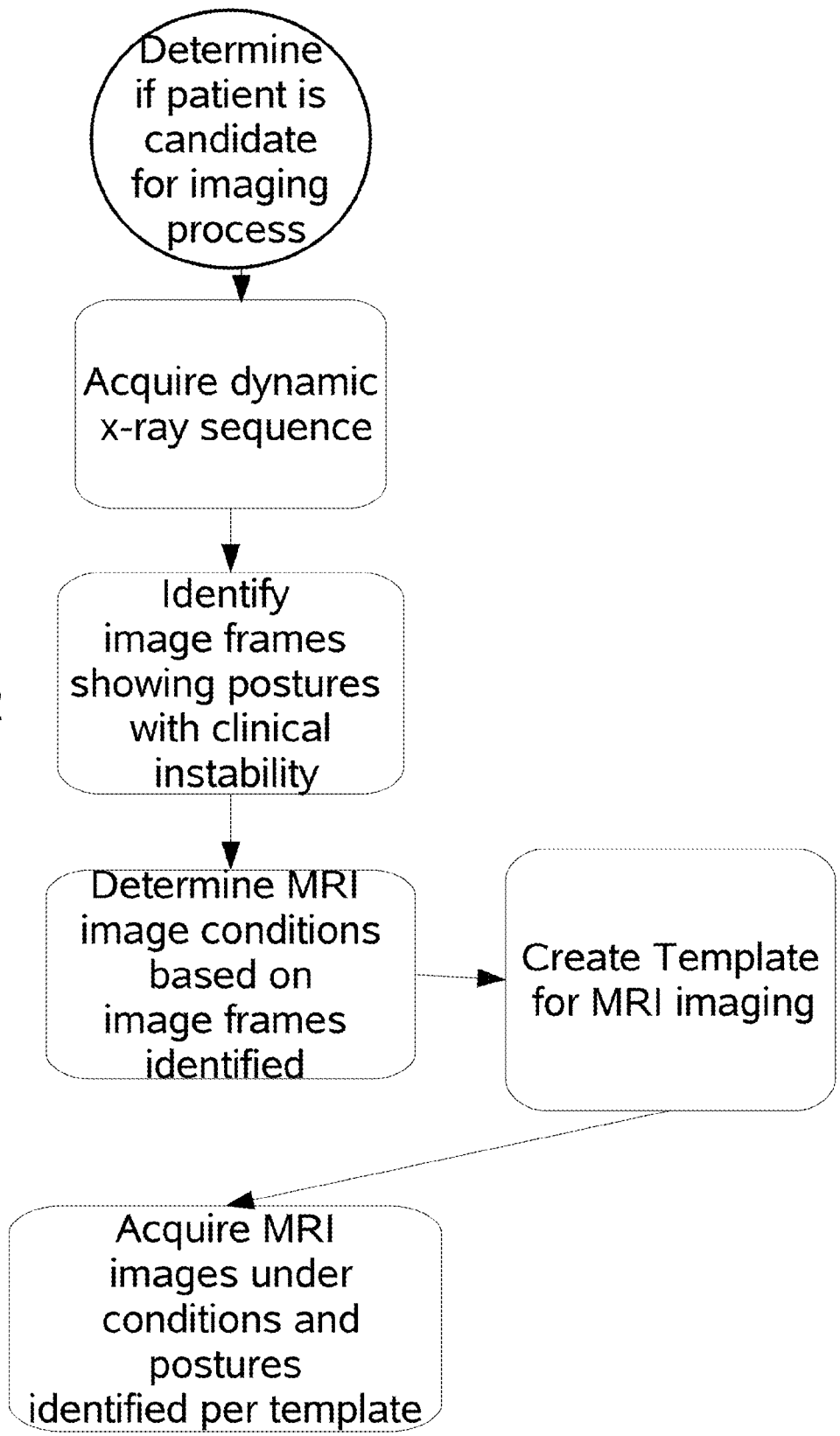
FIG. 2 is a flow chart of a second embodiment of the method

Thus, in another embodiment shown in FIG. 2, an additional step 135 of the preparation of a template guided by motion x-ray findings is to direct MRI image acquisitions. The template may be in an x-ray image that is neutral sagital, flexion, extension and A-P open mouth bending so that the MRI technician can position the patient at the same posture during the MRI acquisition of step 140, as well as acquire the MRI's at the designated slices.

The inventive technique is very effective and reproducible for several reasons. Damage to soft tissue is more likely to be visible under postural loads when the bone movement is abnormal. The abnormality of bone movement will aid in identify the specific soft tissue anatomy that may be damaged. However, the MRI(s) must also be recorded under conditions that are likely to highlight the damage. These conditions will depend on the location of the injury, as the surrounding structure may have inherent low or interfering contrast under some MRI conditions.

Thus, FIG. 9A-13A illustrates such a template wherein the corresponding FIG. 9C-13C are the MRI images of a slices as marked on the template.

Further, imaging parameters also includes a spin sequences, which refers to the precise nature of the magnetic field resonance and decay that is measured. These conditions are well known by the acronyms T1, T2, PDI (proton density image) and the like as indicated in the table. Each Imaging parameter causes different types of cervical or joint tissues to appear lighter or darker in the MRI such that the full detail of the anatomy likely to be involved in each type of pathology in the x-ray sequence can be detected.

The T1 imaging mode reveals bone position and fracture, rim lesion, which is a tearing of a disk from attachment to vertebra body as well as distention of cranial elements through the foramen magnum (opening in skull where spinal cord descends).

In contrast, T2 imaging mode reveal soft tissue, such as ligaments, spinal fluid, nerves, spinal cord, muscle tears, swelling and edema. FSE (fast spin echo) is a subset of the T1 and T2 modes.

Proton density images (PDI) or proton density weighted sequences imaging mode is specifically best suited to reveal ligaments in the cranio-cervical junction ie. (alar, transverse ligament, tectorial membrane, posterior atlanto-occipital membrane and the like). Slice orientation is very import to visualize the alar ligaments consistently. While the gradient echo image (GRE) mode is preferred for acquiring axial (top down) disc images.

Generally, speaking under such appropriate imaging mode/spin conditions normal ligament are typically dark, and expands along their length or breadth at constant and homogenous intensity and thickness. However, if the ligament is damaged, it may appear thin or disappear, if not show an actual tear.

Further, when tissue is damaged it attempts to heal by growing fibrotic cells. However, the fibrotic cells being weaker and not as elastic as the native tissue will in effect be scared, and are frequently visible as lightened area of signal intensity along a dark and continuous ligamentous structure. Sometimes the damaged ligament will thicken where it rubs against a bone due to misalignment from damage to it or another ligament. A few ligaments are particularly prone to such damage not because of initial injury, but because the failure of other ligaments results in their mal-positioning with respect to bone.

Thus the skilled radiologist, surgeon or chiropractor, when presented with the MRI images acquired under conditions in Table I will be utilize their intimate knowledge of normal soft tissue anatomy to recognize the abnormal tissue that is either torn, thinned, scarred or misaligned. It should be appreciated that the invention is not limited to particular spin sequences but may use any current or future MRI imaging modality that may be subsequently discovered.

From such diagnosis of tissue damage by the above method the suitability of various treatment modalities can be evaluated by medical professions, as well as verifying that the patient's complaints of pain are indeed real, as they correlate with nerves that would be affected by the damage. It should be understood that pain can result from either direct damage to soft tissue having sensitive nerve endings (nocioceptors) or because the trauma results in an unstable spine in which bones move and effect various neuro-structure's, nerve roots and spinal cord leading to pain.

Figure 3:
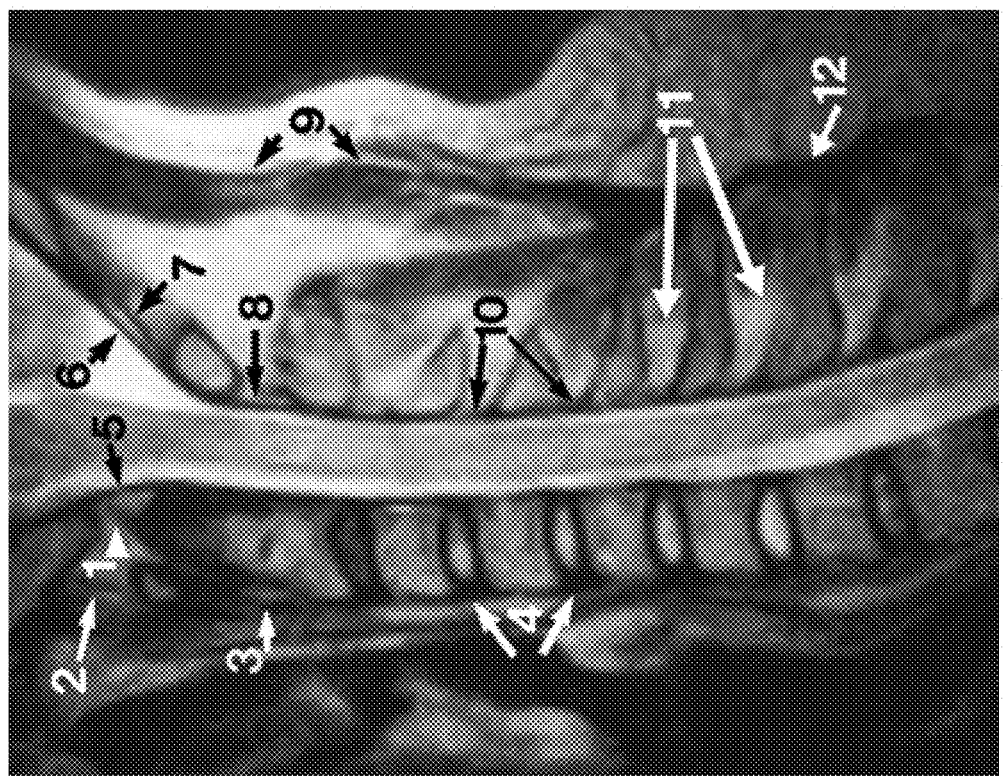
FIG. 3 is a sagittal neutral position MRI of the cervical spine of a healthy patient naming most of the visible anatomy.
Figures 4A, 4B, 4C:

FIG. 3 is a sagittal MRI to illustrate the normal healthy anatomy of the cervical spine, which the numbered arrows point to the following soft tissue structure: 1. Normal apical ligament; 2. Anterior occipitoatlantal membrane; 3. Anterior atlantoaxial membrane; 4. Anterior longitudinal ligament; 5. Tectorial membrane; 6. Dural reflection; 7. Posterior occipitoatlantal membrane; 8. Posterior atlantoaxial membrane; 9. Nuchal ligament; 10. Flaval ligaments; 11. Area of interspinous ligaments; 12. Supraspinous ligament.

FIG. 4-13 now illustrates selected combination of the imaging modes according to Table I that reveal's a variety of soft tissue damage in several patients. FIG. 4A is sagital x-ray frame of a first patient facing forward in an upright neutral posture, while FIG. 4B is a photograph of the patients posture at the time x-ray image of FIG. 4A was acquired. FIG. 4C is the MRI in the same posture and orientation as the X-ray in FIG. 4B, however as the spinal cord and ligaments are now visible the multiple herniated discs bulge outward. This is revealed indirectly by their compression of the spinal cord, as the white lines representing the fluid surrounding the cord has thinned as the disc herniations impinge upon it.

FIG. 5A is sagital x-ray frame of another patient facing forward, in an upright neutral posture while FIG. 5B is a photograph of the patients posture at the x-ray frame of FIG. 5A was acquired. FIG. 5C is the MRI in the same posture and orientation as the X-ray in FIG. 4B, however the herniated discs are more severe than as in FIG. 4C, as the fluid surrounding the cord is no longer visible at the disc herniations.

FIG. 6A is a sagital motion X-ray frame in which the patient is in a flexion posture, which FIG. 6B being the visual image of the patient when the frame of FIG. 6A was recorded. The MRI in FIG. 6C was recorded with the T2 FSE spin sequence at the same flexion posture as FIG. 6A and now shows both Anteriolisthesis (forward slipping) of C4-5 as indicated by arrow 601 and a Torn Posterior Longitudinal Ligament at as indicated by arrow 602.

FIG. 7A is a sagital motion X-ray frame in which the patient is in a flexion posture, which FIG. 7B being the visual image of the patient when frame of FIG. 7A was recorded. The MRI in FIG. 7C was recorded with the T2 FSE spin sequence at the same flexion posture as FIG. 7A and now shows both Anteriolisthesis of C4-5 at arrow 701 and disc/spinal cord compression at arrows 702 and 703.

FIG. 8A is a sagital motion X-ray frame in which the patient is in an extension posture showing Retrolisthesis of C3-4 (backward slipping). The MRI image in FIG. 8C was recorded with a T2 FSE spin sequence and also shows Retrolisthesis of C3-4 at arrow 801 as well as disc/spinal cord compression at arrows 802 and 803.

FIG. 9A is a sagital x-ray frame of a patient in an upright neutral posture and is marked as a template with the series of white lines for MRI slices orientation for coronal images of alar and transverse ligaments. FIG. 9B is a photograph of the patients posture at the time x-ray image of FIG. 9A was acquired. FIG. 9C is the PD weighted MRI image from the middle slice in FIG. 9B, with the arrow pointing to the torn alar ligament.

FIG. 10A is a sagital motion x-ray frame with the patient in an upright posture but in right rotation. FIG. 10B is a photograph of the patients posture at the time x-ray image of FIG. 10A was acquired. FIG. 10A is marked as a template with the series of white lines to show the preferred axial slice orientation for acquiring PD weighted MRI image sequences of axial spots at the craniocervical junction for assessment of the transverse/alar ligament damage. FIG. 10C is the PD weighted MRI image for the slice in FIG. 10A connected by the black arrow that points to it. The white arrow in FIG. 10C lines points to the torn transverse ligament that is now revealed.

FIG. 11A is a sagital motion x-ray frame with the patient in an upright neutral posture. FIG. 11B is a photograph of the patients posture at the time x-ray image of FIG. 11A was acquired. FIG. 11A is marked as a template with the series of white lines to show the preferred axial slice orientation for acquiring a series of MRI's using a T2 FSE spin sequence axial spots at the craniocervical junction for assessment of the transverse/alar ligament damage. FIG. 11C is the corresponding MRI acquired with the patient in the same neutral posture as in FIGS. 11A and 11B. The arrow in FIG. 11C points to the torn transverse ligament.

FIG. 12A is a sagital motion x-ray frame with the patient in an upright flexion posture and is marked as a template with a series of black lines indicated the preferred MRI slice orientation for Axial spot of the intervertebral disc. FIG. 12B is a photograph of the patients posture at the time x-ray image of FIG. 12A was acquired, FIG. 12C is the MRI using GRE spin sequence and obtained at the lower slice in FIG. 12A with the arrow pointing to the region of severe disc herniation with spinal cord and nerve root compression.

Figures 13A, 13B, 13C:
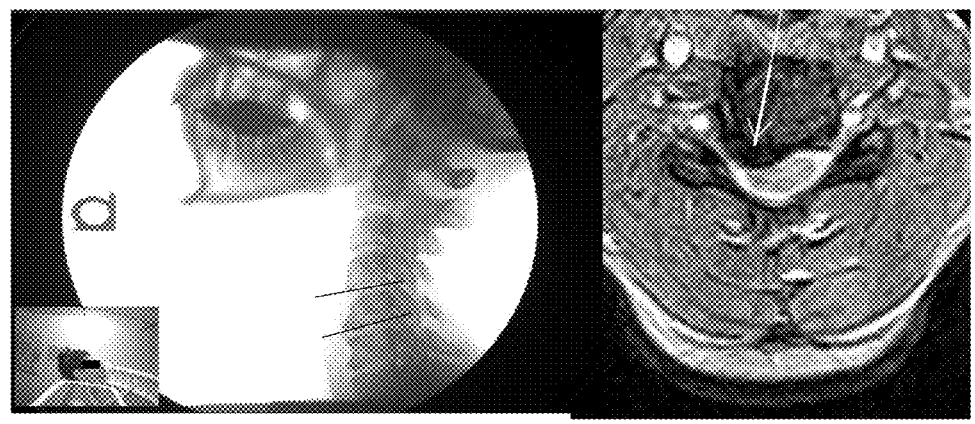

FIG. 13A is a sagital motion x-ray frame with the patient in an upright extension posture and is marked as a template with a series of black lines indicated the preferred MRI slice orientation for Axial spot of the intervertebral disc. FIG. 13B is a photograph of the patients posture at the time the x-ray image of FIG. 13A was acquired. FIG. 13C is the MRI of the lower slice in FIG. 13B acquired with a GRE spin sequence wherein the arrow points to a region of severe disc herniation with spinal cord and nerve root compression.

It should be understood that although the examples provided apply to the cervical spine the various embodiments of the inventive method are applicable to other joints, elbow, knee and like joints with suspected segmental dysfunction.

In another embodiment of the invention it is desirable to record absolute posture in the x-ray motion sequence for optimal or exact patient positioning for the subsequent MRI steps to optimize images of pathoanatomy.

Such methods of reproducing the patient posture in the MRI stage include having the MRI technician or radiologist review the template X-ray images and position the patient as close as possible by visual references. The visual reference can be to the anatomy of the x-ray, but is preferably to a photographic visual light image of the patient recorded simultaneously with the x-ray frame, and generally presented as a smaller magnification image in the corner of the frame. Once the first MRI is acquired at a slice orientation equivalent to the plane of the x-ray image the position of the patient can be adjusted slightly by eye. It is especially preferred that the x-ray and MRI images can be overlaid or fused to assist in making such a visual comparison.

Alternatively, the software described below for image analysis is software may be operative to direct the computer to compare the x-ray and first MRI to determine a goodness of fit of the hard bony anatomy that is visible in both. Once the goodness of fit meets a predetermined level, further MRI imaging can be obtained while the patient maintains the same posture or joint position. Alternatively, when patient is found to have pathology/segmental dysfunction in flexion motion x-ray, a simple goniometer to measure degree of flexion, can assist the MRI technician to reproduce similar posture in MRI.

Additional embodiment of the invention include the partial or full automation of the process sequences using image recognition software that is capable of performing may if not all of the steps described above.

In another embodiment of the invention the analysis is computer aided. The software will encompass using digitized grayscale recognition to automatically access extreme misalignments, capture those images to use to direct proper patient positioning and proper guidance for Dynamic Upright MRI imaging parameters. In other embodiments of the invention software will direct a general purpose computer or a digital signal processor or the like to use digital mensuration in reviewing the motion x-ray sequences to identify the exact images that have met threshold for clinical instability. In general, the software preferably enables the automatic detection, when bony structures have breached a normal positional threshold.

Software method 600 as shown in FIG. 14 in a first step 610, is the acquiring of a sequential plurality of digital x-ray images frames of the joint undergoing motion.

In step 620, each image frame from step 610 is analyzed to identity at least one of perimeter and corners of each bony structure. Software to perform such analysis on grey scale x-ray images is commercially available.

Further, U.S. Pat. Nos. 5,974,165; 7,295,691; all of which are incorporated herein by references, provides further details on methods of detecting bony and other structures in grey scale images by computer means to provide a digital representation for further image processing and analysis described below. As is known in the art, the computer means, or computing means, may include a computer or computer-like object which contains a display, and a processing circuit (e.g., a microcontroller, microprocessor, custom ASIC, or the like) is coupled to a memory and a display. The display may include a display device, such as a touch screen monitor with a touch-screen interface. The computer or computer-like object may include a hard disk, or other fixed, high density media drives, connected using an appropriate device bus, such as a SCSI bus, an Enhanced IDE bus, a PCI bus, etc., a floppy drive, a tape or CD ROM drive with tape or CD media, or other removable media devices, such as magneto-optical media, ect., and a mother board. The motherboard includes, for example, a processor, a RAM, and a ROM, I/O ports which are used to couple to the image sensor, and optional specialized hardware for performing specialized hardware/software functions, such as sound processing, image processing, signal processing, neural network processing, etc., a microphone, and a speaker or speakers. Associated with the computer or computer-like object may be a keyboard for data entry, a pointing device such as a mouse, a mouse pad or digitizing pad. Stored on anyone of the above described storage media (computer readable media), the system and method include programming for controlling both the hardware of the computer and for enabling the computer to interact with a human user. Such programming may include, but is not limited to, software for implementation of device drivers, operating systems, and user applications. Such computer readable media further includes programming or software instructions to direct the general purpose computer to performance in accordance with the system and method. The memory (e.g., including one or more of a hard disk, floppy disk, CDROM, EPROM, and the like) stores x-ray and/or MRI images.

Further, U.S. Pat. No. 5,099,859, which is incorporated herein by references, teaches means for x-ray image acquisition of joints and computer aided characterization of joint abnormalities.

Further, other embodiment of the invention also contemplates alternate means of acquiring a digital representation of joints, and in particular the spine, such as is disclosed in U.S. Pat. No. 6,028,907, which is incorporated herein by reference.

Further, it is preferable that the anatomical identity of each bony structure identified and mapped in step 620 be determined. This determination can be manual, by presenting a subset of the images to a radiologist and request a name or other identity be provided for each discrete bony structure identified in the process. For example, the software can present the radiologist with a grey scale image onto which is overlaid colored outlines or markers of the digital representation of each bony structure determined in step 620, and then prompt for the entry of a name for each structure as it is presented. Alternatively, the determination can be automated wherein the software is operative to make additional calculation to determine a bone identity figure of merit by comparing the digital representation using at least one of formulas and properties in a reference table, and then identify the bone in the table when the calculation yields the highest figure of merit. Such criteria for calculating a figure of merit in the reference table may include, without limitation bone area, proximity of other structures, aspect ratio and the like.

Next in step 630, for each bone structure in each image a bone placement figure of merit (FOM) is calculated to determine if the bony structures have breached a normal positional threshold. Such a threshold calculation may include one or more calculations based on one or a matrix of multiple parameters that may include rotation, displacement and spacing either absolute or with respect to adjacent bones. The bone displacement figure of merit may also take into account widely available diagnostic criteria for any condition. It would also incorporate the AMA Guides for impairment $5^{th}$ edition which define clinical instability. Thus, the higher the figure of merit, the more a bone is displaced from its normal position.

After the calculations in step 630, it then possible to calculate, in step 640, at least one image pathology FOM from the bone displacement FOM for each bone in the image for which the FOM is being calculated. The image pathology FOM may be the raw sum of the bone placement FOM, or a weighted calculation thereof, and optional may only take into account bone displacements that have breached a normal positional threshold.

Using the calculation of steps 630 and 640, it is then possible to determine which x-ray frame show an abnormal pathology and thus direct the further steps of MRI acquisition. Further, to the extent the FOM calculated uses a medical diagnostic criteria, it is possible to also determine the named condition for the abnormal pathology for the direction of MRI acquisition.

Ideally, in step 650 after an image pathology FOM is calculated for each x-ray frame the frames showing the most abnormal pathology, via high image pathology FOM, are selected. Optionally, the radiologist can view these frames in a manner that simultaneously displays the digital representation of the bone to confirm the accuracy thereof, as well as to select patient postures for MRI imaging. To the extent that the software has misidentified or mischaracterized a bone position this can be rectified manually by the radiologist by outline the correction bone position, such as through a pen entry screen, a curser or pointing device and the like, the above FOM calculation re-performed. To the extent that the image pathology FOM has provided a diagnosis for the x-ray frames displace, the radiologist can confirm, update or revise this result as appropriate for further MRI acquisition.

In step 660, the MRI parameters are determined for each patient posture that the radiologist desires to investigate further, or alternatively the MRI parameters can be determined independent of intervention using the postures that results in image frame with the highest image pathology FOM. In this step the pathological diagnosis for the image frame is compared with that in column 1 of Table 1, or a similar table for other disorders to select the MRI parameters in the corresponding row.

In step 670, optionally a template is generated to image the regions surrounding each bone with a high FOM in the selected image frame with an abnormal pathology FOM.

The result of step 670 can be either an image, such as FIG. 9A-13A, with multiple lines shown for MRI slice orientation, or a digital instruction set for MRI acquisition with the MRI parameters being generated based on the corresponding row in Table 1, as well as from the anatomical features that are identified in digital format from step 620.

It should be appreciated that optionally step 600 may includes goniometric measurement of head or neck absolute position in each x-ray frame. This goniometric position of the patients posture is intended to be highly reproducible when positioning the patient for the MRI, and would thus also be includes in MRI instruction set that results from step 670.

Thus, in step 680 the MRI's are acquired per the MRI template of Step 670, with the patient in the posture determined by the frames selected in step 650.

The above process preferably creates or deploys the following data files or data structure of which the content is described below:

For each frame in the series of dynamic x-rays images there is a digital version that is a Bit map or vector representation of image, that is photon intensity versus position, as well as a frame reference indicator so the frame can be indexed with respect to adjacent images in the sequence. Further, U.S. Pat. No. 6,799,06, which is incorporated herein by reference, teaches additional means of automated image feature extraction and digitally representing cartilage structure in MRI images for the purposes of accessing the disease state, which are generally applicable to bone structures as well as further steps of quantifying the damage to soft tissue that is ultimately imaged by MRI in step 680.

Within or associated with each referenced frame is a data record of the identity of each bone structure detected by the image analysis process as well as a geometric representation of the bone as a series of at least 3 coordinate points or vectors, which may represent corners or the perimeter.

Further associated with each bone in each image are bone pathology FOM, and optionally an identity for each bone, such a name, number or combination thereof.

Further associated with each image frame is an image pathology FOM, an optional image pathology diagnosis.

It should be understood that the digital reference to an image frame does not preclude various data compression formats, such as JPEG, MPEG and the like, not does the reference to the calculation of image pathology with respect to each x-ray frame mean that absolutely each frame is analyzed, as it is expected to eliminate frame's that show little change or down select a smaller number of representative x-ray frames by pre-processing and other means to lessen the calculation burden.

To the extent that the MRI parameters are not determined manually after step 650, it is further desirable that the data file or record of image frame selected for obtaining a corresponding MRI also have associated therewith the MRI acquisitions parameters, such as slice orientation, spin sequence parameters and the like as described above. Further, to the extent that it is desirable to obtain multiple MRI at different postures, it is also desirable that the master patient data file contain or associate these and other parameters to each x-ray frame of interest, meaning it has an identified pathology or serves as a normal state references subject to further MRI acquisitions.

Optionally, the data set for each image frame of interest also include a posture coordinate set which contains the goniometric measurement of one or more external positions of a characteristic external anatomy that when reproduced in the MRI chamber uniquely position the patient in the same posture as the X-ray acquisition step. Of course it should be appreciated that another aspect of the invention is an imaging device or machine that acquires both the x-ray and MRI images while the patient is seated or otherwise disposed in the same chamber of the device so as to minimize the posture reproducibility error. Such a generic MRI machine 1500 is schematically illustrated in a plan section in FIG. 15A, the patient 10, or a portion thereof is situated in zone or cavity 1501 to be exposed to a magnetic field 1502 from the MRI magnet source 1505. Pick up coils are omitted from the figures for simplicity of illustration, as are other components well understood to one of ordinary skill in MRI technology. The MRI instrument 1500 having a cavity 1501 for receiving a patient 10 that is open on two or more opposing sides, an x-ray source 1510 is disposed to irradiate a patent in the cavity 1501 of the MRI from a first of the two or more open sides such that the spatial attention of x-rays by area x-ray detector 1515, disposed on a side opposite said x-ray source 1510 can continuously acquire a plurality of x-ray images of the patient during the initial phase of their movement as described above. Preferably a digital camera 1520 simultaneously acquires visual images of the patient to aid in posture reproduction as described further below.

MRI machine 1500 also includes a control unit, power and image processing unit 1530 connected in power and/or signal communication with each of the MRI magnet source 1505, x-ray source 1510, x-ray detector 1515 and preferably also the optional digital camera 1520.

However, since the x-ray image are acquired dynamically while the patient move the limb or joint, there will still be a need reproduce a particular position that corresponds to a posture that was held for a mere instant during the course of the x-ray acquisition process.

Figures 15A, 15B:
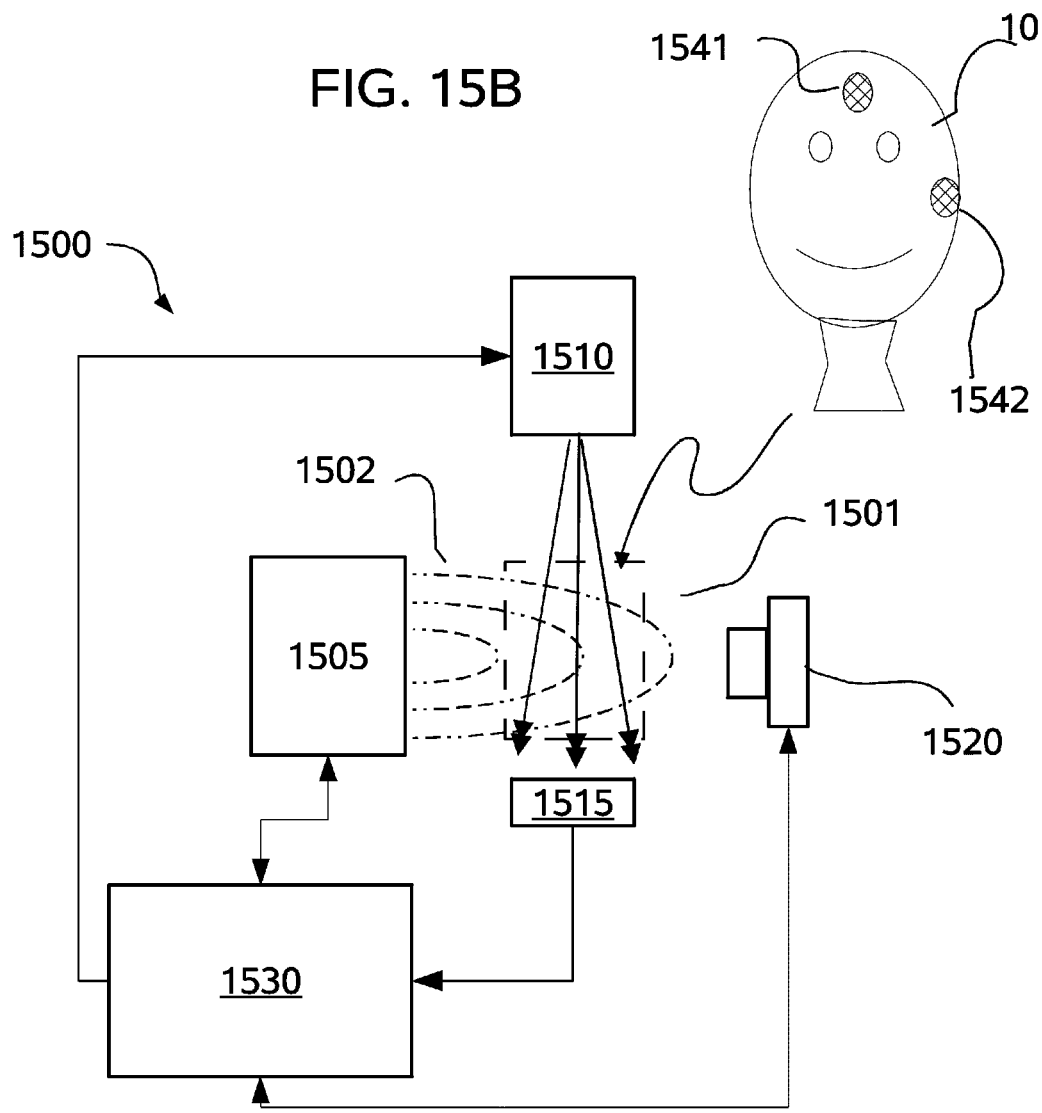
FIG. 15A is a plan section view to schematically illustrate an embodiment of an apparatus for carrying out the imaging process.
FIG. 15B is a schematic illustration of a method of posture tracking for use with the inventive method.

FIG. 15B illustrates a configuration for tracking posture of a patient 10, by placing marking 1541 and 1542 on select portion of the head, face or neck. The marking can be imaged with the digital camera in synchronization with the dynamic x-ray frame acquisition, hence then by associating each x-ray frame with image coordinates for the marking 1541, 1442 and the like, the same posture can be verified by using the digital camera and image analysis software to confirm the markings have the same image coordinates.

In additional, for calculating bone pathology, bone identity and image pathology FOM's it is desirable to utilize additional data files so that comparison can be made to a normal or nominal pathology and the FOM calculated. Further to the extent that certain MRI imaging be conducted automatically, it is also desirable that process 600 also identify reference topography were desired to define the slice orientation precisely, based on the first or any earlier acquired MRI after the patient is placed in the designated posture.

In addition, there is a data file representing the information in Table 1 and the like, so that the proper MRI conditions are selected based on the abnormal pathology found in the particular image frames by the process 600. Data file for image pathology FOM calculation and comparison for each bone in each image pathology that requires a particular set of MRI imaging parameters While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

TABLE 1

| | | MRI | MRI Imaging parameters | | | |
|---|---|---|---|---|---|---|
| | | Image plane or slice | Patient position(s) or posture | Slice orientation(s) | Slice thickness | Imaging parameters |
| Neutral Sagital Motion X-Ray clip Findings | If patient is found to have a loss of the cervical lordosis, straightening, curve reversal, buckling, signs of angulation or listhesis. Note: structures that are found and can be evaluated: Ligaments found to stretch or fail are the anterior longitudinal ligament, posterior longitudinal ligament, ligamentum flavum, Facet capsular ligament, Interspinous ligament, supra spinous ligament, Nuchal ligament, alar ligament, transverse ligament, apical ligament, tectorial membrane, posterior atlanto occipital membrane, posterior atlanto axial membrane | Sagital | Neutral | Parallel to the cervical spine, with stack oriented thru the center and sides of the dens of C2 | 3 mm | T1, T2 FSE. When necessary Proton Density weighted image if suspected ligamentous damage. |
| | | Axial | Neutral | Slice orientation parallel to the endplates with stack starting above, going thru and below the endplates | 3 mm | GRE |
| Neutral Sagital | Disc Space angulation | Axial | Neutral | If angulation is present, slice thru the center of the disc. Split the difference of the angulation of upper and lower vertebral endplate's for slice orientation | 3 mm | GRE |
| A-P open mouth Motion X-ray Clips | Suspected alar, accessory or transverse ligament failure | Coronal at the craniocervical junction | Neutral | Slice orientation approximately 10-15 degrees posterior to the superior/posterior position of the tip of the dens of C2 | 2.8 mm | Proton Density weighted sequence |

TABLE 1-continued

| | MRI | MRI Imaging parameters | | | | |
|---|---|---|---|---|---|---|
| | | Image plane or slice | Patient position(s) or posture | Slice orientation(s) | Slice thickness | Imaging parameters |
| A-P open mouth Motion X-ray Clips | Suspected alar, or transverse ligament failure | Axial spot | Neutral | Slice orientation somewhat perpendicular to the tip of the dens of C2, starting above the foramen magnum to the middle of the body of C2 | 2.8 mm | Proton Density weighted sequence |
| 1. Flexion sagital motion X-ray clips | Listhesis or interspinous fanning, angulation consistant with failure of the PLL, Ligamentum flavum, facet joint capsule, interspinous ligament and nuchal or supraspinous ligament | Sagital Flexion | Flexion | Slice orientation(s) Parallel to the cervical spine, with stack oriented thru the center and sides of the dens of C2 | 3 mm | |
| Flexion Sagital motion X-ray clip | | Sagital Flexion | Flexion axial spot when disc pathology found such as angulation, protrusion/herniation | Slice orientation parallel to the endplates with stack starting above, going thru and below the endplates | | |
| Sagital Extension motion X-ray clip | | Sagital Extension | Extension axial spot when disc pathology found such as angulation, protrusion/herniation | Slice orientation parallel to the endplates with stack starting above, going thru and below the endplates | | |
| Sagital Extension motion X-ray clip | | Sagital Extension | Extension | Parallel to the cervical spine, with stack oriented thru the center and sides of the dens of C2 | | |

The invention claimed is:

1. A medical imaging method for joints in living creatures, the method comprising the steps of:
   a. acquiring a dynamic sequence of x-ray images of at least one joint of a living creature over a range of motion,
   b. analyzing the dynamic x-ray image frames to identify at least a location within one posture position presenting a possible abnormal pathology,
   c. determining Magnetic Resonance Imaging (MRI) parameters for imaging the possible abnormal pathology in greater detail than the x-ray images,
   d. acquiring at least one series of multiple MRI images at positions and locations with the potential abnormal pathology with said parameters wherein the MRI parameters include obtaining one or more MRI images at the same posture that presented the possible abnormal pathology, wherein the MRI images in the at least one series are of parallel spaced apart planes in the living creature, each spaced apart plane being separated from the most adjacent spaced apart plane by a spacing of not more than 3 mm.

2. A medical imaging method for joints in living creatures according to claim 1 wherein at least one joint is the human cervical spine and the living creature is a human being disposed in an upright posture.

3. A medical imaging method for joints in living creatures according to claim 2 wherein the range of motion comprises at least one of flexion, extension and rotation of the head and neck.

4. A medical imaging method for joints in living creatures according to claim 3 wherein said step of acquiring a dynamic sequence of x-ray images and acquiring MRI images is carried out in an instrument having a cavity for receiving a patient that is open on two or more opposing sides, wherein an x-ray source disposed to irradiate a patent in the cavity of the MRI from a first of the two or more open sides, and an x-ray detector disposed on a side opposite said x-ray source for continuously acquiring a plurality of x-ray images of the patient.

5. A medical imaging method for joints in living creatures according to claim 4 wherein said step of acquiring a dynamic sequence of x-ray images and acquiring MRI images is carried out in an instrument further comprising a patient support surface wherein the patient is in an upright position in the MRI cavity.

6. A medical imaging method for joints in living creatures according to claim 4 wherein during said step of acquiring a dynamic sequence of x-ray images the x-ray detector is operative to continuously acquire digital X-ray images as discrete image frames for further analysis to determine MRI imaging parameters.

7. A medical imaging method for joints in living creatures according to claim 1 wherein said step of acquiring a dynamic sequence of x-ray images is carried out in an instrument having means to reproducibly position the patient in the same posture for the acquisition of multiple MRI images in that posture.

8. A medical imaging method for joints in living creatures according to claim 7 further comprising the step of reproducibly positioning the patient in the same posture for the acquisition of multiple MRI images wherein the means to reproducibly position comprises a digital camera to simultaneously acquire visual image frames in synchronization with x-ray image frames wherein a posture coordinate set is determined from visual markers placed on the patient.

9. A medical imaging method for joints in living creatures according to claim 1 further comprising the step of marking one of more dynamic x-ray image frames are with multiple lines to identify the parallel spaced apart planes for which the multiple MRI images are acquired.

10. A medical imaging method for joints in living creatures according to claim 1 wherein said step of analyzing the dynamic x-ray image frames further comprises the step of identifying the possible abnormal pathology with a computing means.

11. A medical imaging method for joints in living creatures according to claim 10 wherein during said step of identifying the possible abnormal pathology with the computing means said computing means is further operative to:
   a) analyze a sequence of digital x-ray image of a joint of a living creature in motion to:
      i. identifying the boney structures in each image in the sequence;
      ii. compare for each image in the sequence the relative position of at least one reference position on each bony structure with respect to another reference position on each adjacent bony structure to develop at least one relative displacement parameter of the reference position of each bony structure;
      iii. compare each relative displacement parameter for each boney structure against a nominal reference value from a first reference table to develop a first figure of merit representing the abnormality for each boney structure in each image frame;
      iv. develop a second figure of merit for the abnormal pathology of each image frame from the cumulative values of the first figure of merit associated with each boney structure in the image frame;
   b. select at least one image frame based on the second figure of merit for acquiring one of more MRI images wherein the joint is in the same posture as in the image frame selected from the second figure of merit;
   c. determine the MRI parameters for imaging the possible abnormal pathology in greater detail than the x-ray images.

12. A medical imaging method for joints in living creatures according to claim 10 wherein during said step of identifying the possible abnormal pathology with the computing means, said computing means is operative to analyze each digital x-ray image frame for determining MRI imaging parameters.

13. A medical imaging method for joints in living creatures according to claim 10 wherein during said step of identifying the possible abnormal pathology with the computing means, the computing means is further operative to compare the posture of a patient in one or more x-ray image frames to at least one MRI image to confirm the patient has the same posture in the X-ray images of interest before acquiring one or more MRI images in that posture.

14. A medical imaging method for joints in living creatures according to claim 10 wherein during said step of identifying the possible abnormal pathology with the computing means, the computing means is operative to associate a posture coordinate set for one or more X-ray image frames of interest to confirm the same posture of the patient before acquiring multiple MRI images in that posture.

15. A non-transient computer-readable medium having stored thereon software that is operative to direct a general purpose computer to carry out the steps of:
   a. analyzing a sequence of digital x-ray image of a joint of a living creature in motion to:
      i. identifying the boney structures in each image, in the sequence
      ii. comparing for each image in the sequence the relative position of at least one reference position on each bony structure with respect to another reference position on each adjacent bony structure to develop at least one relative displacement parameter of the reference position of each bony structure,
      iii. comparing each relative displacement parameter for each boney structure against a nominal reference value from a first reference table to develop a first figure of merit representing the abnormality for each boney structure in each image frame,
      developing a second figure of merit for the abnormal pathology of each image frame from the cumulative values of the first figure of merit associated with each boney structure in the image frame,
   b. selecting at least one image frame based on the second figure of merit for acquiring one of more MRI images wherein the joint is in the same posture as in the image frame selected from the second figure of merit,
   c. determining the MRI parameters for imaging the possible abnormal pathology in greater detail than the x-ray images from a third reference table.

16. A non-transient computer-readable medium having stored thereon software according to claim 15 that is further operative to mark one of more dynamic x-ray image frames with multiple lines to provide a series of slice orientations for the MRI imaging parameters.

17. A non-transient computer-readable medium having stored thereon software according to claim 15 that is further operative direct an MRI machine to automatically acquire images at the MRI parameters.

18. A non-transient computer-readable medium having stored thereon software according to claim 15 that is further operative to confirm the joint is in the same posture during a subsequent step of MRI imaging in at least one of the same and a different MRI machine.

19. A non-transient computer-readable medium having stored thereon software according to 18 wherein the at least one joint is the human cervical spine and the living creature is a human being disposed in an upright posture.

20. A non-transient computer-readable medium having stored thereon software according to 15 that is further operative to identify reference topograpy in MRI images thus acquired to define the slice orientation for additional MRI images to be subsequently acquired.

21. A non-transient computer-readable medium having stored thereon software according to claim 20 wherein the range of motion comprises at least one of flexion, extension and rotation of the head and neck.

* * * * *